United States Patent
Labbé

(10) Patent No.: US 12,205,566 B2
(45) Date of Patent: Jan. 21, 2025

(54) DEVICE, METHOD, AND MEDIUM FOR INTEGRATING AUDITORY BEAT STIMULATION INTO MUSIC

(71) Applicant: Lucid Inc., Toronto (CA)

(72) Inventor: Aaron Labbé, Toronto (CA)

(73) Assignee: Lucid Inc., Toronto (CA)

( * ) Notice: Subject to any disclaimer, the term of this patent is extended or adjusted under 35 U.S.C. 154(b) by 637 days.

(21) Appl. No.: 17/608,113

(22) PCT Filed: May 1, 2020

(86) PCT No.: PCT/CA2020/050585
§ 371 (c)(1),
(2) Date: Nov. 1, 2021

(87) PCT Pub. No.: WO2020/220140
PCT Pub. Date: Nov. 5, 2020

(65) Prior Publication Data
US 2022/0262332 A1    Aug. 18, 2022

Related U.S. Application Data

(60) Provisional application No. 62/842,196, filed on May 2, 2019.

(51) Int. Cl.
*G10H 1/12* (2006.01)
*G10H 1/00* (2006.01)
(Continued)

(52) U.S. Cl.
CPC .............. *G10H 1/12* (2013.01); *G10H 1/0008* (2013.01); *G10H 5/002* (2013.01); *H04S 1/007* (2013.01);
(Continued)

(58) Field of Classification Search
CPC ........ G10H 1/12; G10H 1/0008; G10H 5/002; G10H 2210/066; G10H 2210/081; G10H 2210/375; H04S 1/007
(Continued)

(56) References Cited

U.S. PATENT DOCUMENTS 7,778,718 B2 * 8/2010 Janke ....................... H04R 3/04
381/103
2009/0019995 A1 * 1/2009 Miyajima ............ G10H 1/0025
84/625
(Continued)

FOREIGN PATENT DOCUMENTS

EP    2103288        9/2009
EP    2103288 A2 *  9/2009  ............. A61B 5/486
(Continued)

OTHER PUBLICATIONS

"Japanese Application Serial No. 2021-565131, Notification of Reasons for Rejection mailed Sep. 5, 2023", W English Translation, 9 pgs.
(Continued)

*Primary Examiner* — Christina M Schreiber
(74) *Attorney, Agent, or Firm* — Schwegman Lundberg & Woessner, P.A.

(57) ABSTRACT

A device, method, and medium for integrating monaural and binaural beats into music are provided. The music is analyzed to determine key, root tone, and spectral range. It is then remixed with monaural beats and/or binaural beats at frequencies based on a desired entrainment frequency and the root tone and lowest dominant frequency range of the music. Additional harmonics of the beats in higher octaves may be integrated into the music as well using mixing and/or equalization.

20 Claims, 7 Drawing Sheets

(51) Int. Cl.
  *G10H 5/00* (2006.01)
  *H04S 1/00* (2006.01)
(52) U.S. Cl.
  CPC . *G10H 2210/066* (2013.01); *G10H 2210/081* (2013.01); *G10H 2210/375* (2013.01)
(58) Field of Classification Search
  USPC .......................................................... 84/625
  See application file for complete search history.

(56) References Cited

U.S. PATENT DOCUMENTS

| | | | | |
|---|---|---|---|---|
| 2010/0239096 | A1* | 9/2010 | Jeon | H04R 3/04 381/1 |
| 2014/0350706 | A1* | 11/2014 | Morishima | G10K 15/04 700/94 |
| 2016/0055842 | A1* | 2/2016 | DeFranks | G10K 11/175 381/66 |
| 2021/0030308 | A1* | 2/2021 | Grace | A61B 5/486 |
| 2022/0262332 | A1* | 8/2022 | Labb | G10H 1/12 |

FOREIGN PATENT DOCUMENTS

| | | | | |
|---|---|---|---|---|
| EP | 3047478 B1 | * | 10/2018 | ............ G06F 16/60 |
| EP | 3963569 | | 3/2022 | |
| JP | 2017111414 | | 6/2017 | |
| JP | 2017111414 A | * | 6/2017 | ............ A61B 5/024 |
| JP | 2022531432 | | 7/2022 | |
| JP | 2022531432 A | * | 7/2022 | |
| JP | 7537720 B2 | | 8/2024 | |
| WO | 2017086353 | | 5/2017 | |
| WO | WO-2017086353 A1 | * | 5/2017 | |
| WO | WO-2019040524 A1 | * | 2/2019 | ............ G09B 5/04 |
| WO | 2020220140 | | 11/2020 | |
| WO | WO-2020220140 A1 | * | 11/2020 | ........... G10H 1/0008 |

OTHER PUBLICATIONS

"Japanese Application Serial No. 2021-565131, Response filed Sep. 19, 2023 to Notification of Reasons for Rejection mailed Sep. 5, 2023", with machine translation, 23 pgs.
"Japanese Application Serial No. 2021-565131, Notification of Reasons for Rejection mailed Oct. 10, 2023", with machine translation, 8 pgs.
"Japanese Application Serial No. 2021-565131, Examiners Decision of Final Refusal mailed Jan. 30, 2024", with English translation, 8 pgs.
"Japanese Application Serial No. 2021-565131, Response filed Jan. 4, 2024 to Notification of Reasons for Rejection mailed Oct. 10, 2023", w English claims, 18 pgs.
"Japanese Application Serial No. 2021-565131, Response filed May 27, 2024 to Examiners Decision of Final Refusal mailed Jan. 30, 2024", w English claims, 21 pgs.
"International Application Serial No. PCT CA2020 050585, International Search Report mailed Jul. 21, 2020", 3 pgs.
"International Application Serial No. PCT CA2020 050585, Written Opinion mailed Jul. 21, 2020", 3 pgs.
"International Application Serial No. PCT CA2020 050585, International Preliminary Report on Patentability mailed Nov. 11, 2021", 5 pgs.
"European Application Serial No. 20798013.7, Extended European Search Report mailed Jan. 26, 2023", 4 pgs.
"European Application Serial No. 20798013.7, Communication Pursuant to Article 94(3) EPC mailed Feb. 7, 2023", 5 pgs.
"European Application Serial No. 20798013.7, Voluntary Amendment filed Oct. 30, 2021", 95 pgs.
"Japanese Application Serial No. 2021-565131, Written Amendment filed Jan. 4, 2022", with English translation, 15 pgs.
European Application Serial No. 20798013.7, Communication Pursuant to Article 94(3) EPC mailed Jul. 31, 2024, 4 pgs.
European Application Serial No. 20798013.7, Response filed Aug. 9, 2024 to Communication Pursuant to Article 94(3) EPC mailed Jul. 31, 2024, 10 pgs.

* cited by examiner

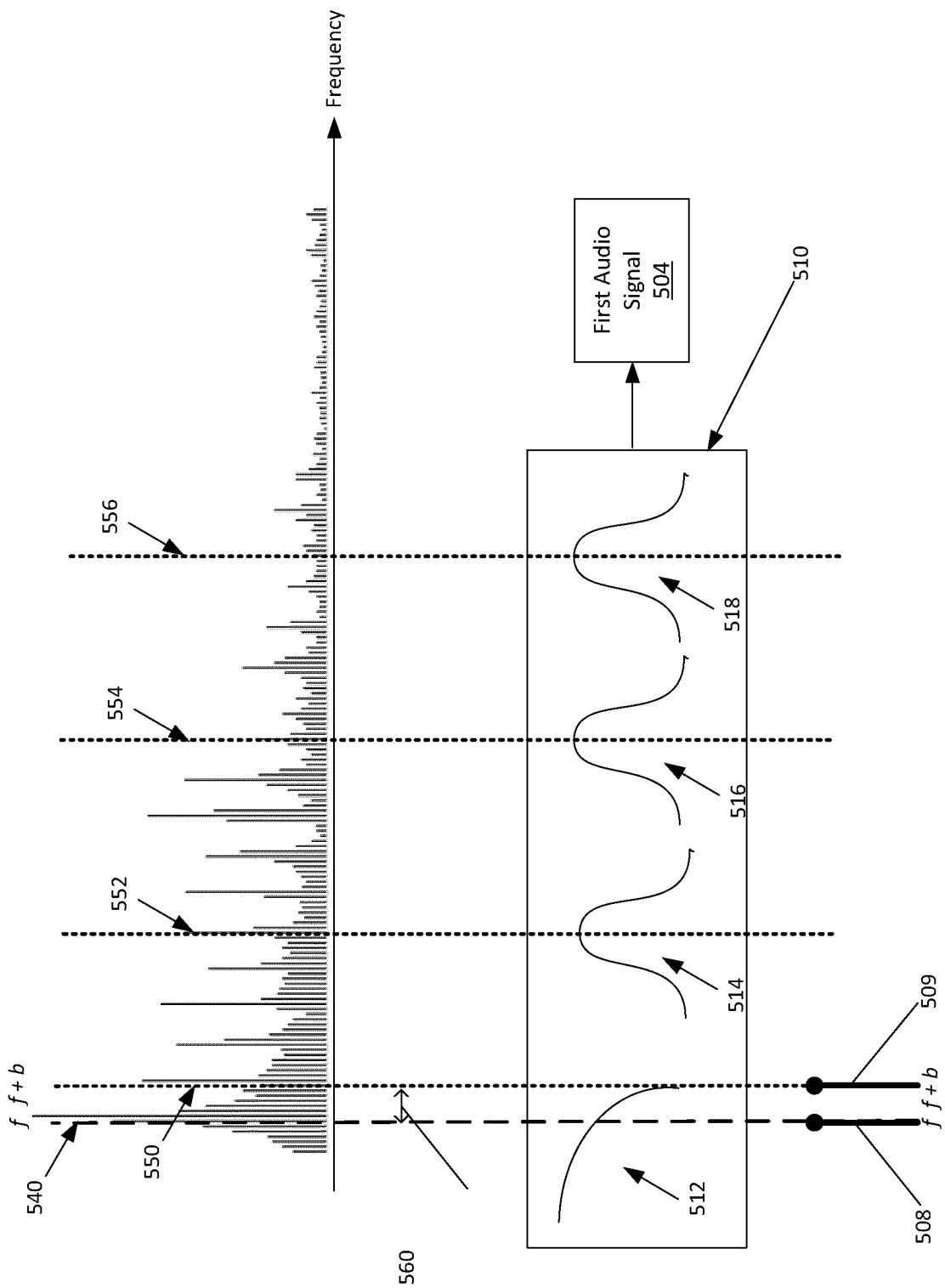

DEVICE, METHOD, AND MEDIUM FOR INTEGRATING AUDITORY BEAT STIMULATION INTO MUSIC

RELATED APPLICATIONS

This application is a national phase entry of international application PCT/CA2020/050585 filed May 1, 2020. This application claims priority to U.S. Provisional Patent Application No. 62/842,196 filed May 2, 2019.

FIELD

At least some example embodiments relate to beat stimulation, and in particular to integrating binaural and monaural beats into music.

BACKGROUND

Auditory beat stimulation is a technique for modifying human or animal brainwave patterns using auditory stimuli. The auditory stimuli consist of two sine waves of nearby but distinct frequencies with constant amplitudes. The stimulus may be presented as a "monaural beat" by presenting the two sine waves simultaneously to both ears of a subject, or as a "binaural beat" by presenting one of the two sine waves to each ear separately.

In both cases, the frequency difference between the two sound waves (the "delta" frequency) is perceived as a "beat" having a frequency of delta. In the case of monaural beats, the delta-frequency beat is an actual physical beat, i.e. an amplitude-modulated (AM) signal having regularly-timed sound amplitude peaks, and is perceived as such by a subject. In the case of binaural beats, the delta frequency difference between the sine wave presented to the subject's left ear and the sine wave presented to the subject's right ear is subjectively perceived as a beat having a frequency of delta. Because binaural beats are not physical properties of the sound waves in any one spatial location, but are instead a percept generated by the subject's brain combining stimuli received by the subject's two ears, subjects sometimes describe binaural beats as being located inside their heads.

Thus, if two sine waves of sound are generated at 300 Hz and 320 Hz, they may either be summated and presented to both ears of a user simultaneously to produce a monaural beat of (delta=320−300=20 Hz), or the 300 Hz signal may be provided to the left ear of a subject (using e.g. stereo headphones) and the 320 Hz signal to the right ear of the subject to create a binaural beat of 20 Hz.

Auditory beat stimulation (ABS) using monaural and binaural beats has been the subject of research as a technique for brainwave entrainment. Evidence suggests that presenting a subject with a monaural or binaural beat may entrain the subject's brain to produce a brainwave spike at the delta frequency of the beat, e.g. in the example above a subject exposed to the 20 Hz beat would be entrained to exhibit a brainwave spike at 20 Hz. Further research suggests that brainwave entrainment may be effective in regulating or altering attention, mood, anxiety, vigilance, memory, and/or other cognitive processes. See e.g. the comparative literature study by Chaieb et al., "Auditory Beat Stimulation and its Effects on Cognition and Mood States", Frontiers in Psychiatry, Vol. 6, 2015, https://www.frontiersin.org/article/10.3389/fpsyt.2015.00070 (hereinafter "the Chaieb paper", which is hereby incorporated by reference in its entirety).

The nature of binaural and monaural beats is musically dissonant due to the simultaneous presence or perception of slightly mismatched frequencies in the stimulus. Subjects sometimes report discomfort when exposed to ABS due to the dissonant noise. This discomfort may limit subjects' willingness to expose themselves to ABS often enough and for long enough periods to achieve the desired effects.

SUMMARY

The present disclosure describes example devices, methods and non-transitory media for integrating binaural and monaural beats with pre-existing or generated music. In some embodiments, the beats may be masked by the music to reduce the perception of dissonant noise by a subject or to reduce the conscious perception of the beats.

Example embodiments are directed to a method for integrating auditory beat stimuli into music, comprising identifying a root tone frequency of an unmodified music signal; selecting a first beat frequency; generating a first beat component having a frequency equal to the root tone frequency; generating a second beat component having a frequency equal to the root tone frequency shifted by the first beat frequency; and mixing the unmodified music signal with the first beat component and second beat component to produce a modified music signal.

According to a further aspect which can be combined with other embodiments disclosed herein, the method further comprises generating a first audio signal comprising a first portion of the unmodified music signal lying within a first frequency range, the first frequency range being based on a first filter frequency, the first filter frequency being equal to the root tone frequency shifted by the first beat frequency, wherein mixing the unmodified music signal with the first beat component and second beat component comprises mixing the unmodified music signal with the first audio signal, the first beat component, and the second beat component to produce the modified music signal.

According to a further aspect which can be combined with other embodiments disclosed herein, the method further comprises identifying a lowest dominant frequency range of the unmodified music signal, wherein the root tone frequency is based on the lowest dominant frequency range.

According to a further aspect which can be combined with other embodiments disclosed herein, the method further comprises identifying a key of the unmodified music signal, the key comprising a plurality of scale degrees, each scale degree having a scale degree frequency, wherein selecting the first beat frequency comprises selecting a first scale degree frequency of the key based on the proximity of the first scale degree frequency to a desired beat frequency.

According to a further aspect which can be combined with other embodiments disclosed herein, the first frequency range comprises a low-pass frequency range with a high-end cut-off frequency equal to the first filter frequency.

According to a further aspect which can be combined with other embodiments disclosed herein, the first audio signal further comprises one or more additional portions of the unmodified music signal lying within one or more additional frequency ranges, the one or more additional frequency ranges being one or more frequency bands centered on one or more additional filter frequencies, each of the one or more additional filter frequencies being equal to the first filter frequency times an integer multiplier.

According to a further aspect which can be combined with other embodiments disclosed herein, each integer multiplier is a power of four.

According to a further aspect which can be combined with other embodiments disclosed herein, the one or more additional filter frequencies comprise three additional filter frequencies having respective integer multipliers of 4, 16, and 64 respectively.

According to a further aspect which can be combined with other embodiments disclosed herein, the modified music signal comprises a stereo music signal having a first channel and a second channel; the first frequency range comprises a band-pass frequency range with a center frequency equal to the first filter frequency; and mixing the unmodified music signal with the first audio signal, the first beat component, and the second beat component comprises mixing the unmodified music signal with the second beat component and first audio signal to generate the first channel; the method further comprising: generating a second audio signal comprising a second portion of the unmodified music signal lying within a second frequency range, the second frequency range comprising a band-pass frequency range with a center frequency equal to a second filter frequency, the second filter frequency being equal to the root tone frequency; and mixing the unmodified music signal with the first beat component and second audio signal to generate the second channel.

According to a further aspect which can be combined with other embodiments disclosed herein, the first audio signal further comprises a third portion of the unmodified music signal lying within a third frequency range, the third frequency range comprising a low-pass frequency range with a high-end cut-off frequency equal to a third filter frequency, the third filter frequency being equal to half of the root tone frequency shifted by the first beat frequency; and the second audio signal further comprises a fourth portion of the unmodified music signal lying within a fourth frequency range, the fourth frequency range comprising a low-pass frequency range with a high-end cut-off frequency equal to a fourth filter frequency, the fourth filter frequency being equal to half of the root tone frequency.

According to a further aspect which can be combined with other embodiments disclosed herein, the first audio signal further comprises one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency times an integer multiplier, shifted by the first beat frequency; and the second audio signal further comprises one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

According to a further aspect which can be combined with other embodiments disclosed herein, each integer multiplier is a power of four.

According to a further aspect which can be combined with other embodiments disclosed herein, the first audio signal further comprises: a third portion of the unmodified music signal lying within a third frequency range, the third frequency range comprising a low-pass frequency range with a high-end cut-off frequency equal to a third filter frequency, the third filter frequency being equal to half of the root tone frequency shifted by the first beat frequency; and one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency times an integer multiplier, shifted by the first beat frequency; and the second audio signal further comprises: the third portion of the unmodified music signal; and one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

According to a further aspect which can be combined with other embodiments disclosed herein, the first audio signal further comprises: a third portion of the unmodified music signal lying within a third frequency range, the third frequency range comprising a low-pass frequency range with a high-end cut-off frequency equal to a third filter frequency, the third filter frequency being equal to half of the root tone frequency shifted by the first beat frequency; and one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency shifted by the first beat frequency, times an integer multiplier; and the second audio signal further comprises: the third portion of the unmodified music signal; and one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

According to a further aspect which can be combined with other embodiments disclosed herein, the first audio signal further comprises: a third portion of the unmodified music signal lying within a third frequency range, the third frequency range comprising a low-pass frequency range with a high-end cut-off frequency equal to a third filter frequency, the third filter frequency being equal to one quarter of the root tone frequency shifted by the first beat frequency; and one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency shifted by the first beat frequency, times an integer multiplier; and the second audio signal further comprises: the third portion of the unmodified music signal; and one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

According to a further aspect which can be combined with other embodiments disclosed herein, a device is provided for integrating auditory beat stimuli into music, comprising: a root tone detector for identifying a root tone of an unmodified music signal; a first oscillator for generating a first beat component having a frequency equal to a root tone frequency, the root tone frequency being based on the root tone; a second oscillator for generating a second beat component having a frequency equal to the root tone frequency shifted by a first beat frequency; and a mixer for mixing the unmodified music signal with the first beat component and second beat component to produce a modified music signal.

According to a further aspect which can be combined with other embodiments disclosed herein, the device further comprises an equalizer for applying a first filter to the unmodified music signal to generate a first audio signal comprising a first portion of the unmodified music signal lying within a first frequency range, the first frequency range being based on a first filter frequency, the first filter frequency being equal to the root tone frequency shifted by the first beat frequency, wherein the mixer is further configured to mix the unmodified music signal with the first audio signal, the first beat component, and the second beat component to produce the modified music signal.

According to a further aspect which can be combined with other embodiments disclosed herein, the device further comprises a spectral analyzer for identifying a lowest dominant frequency range of the unmodified music signal,
wherein the root tone frequency is further based on the lowest dominant frequency range.

According to a further aspect which can be combined with other embodiments disclosed herein, the root tone detector is further configured to identify a key of the unmodified music signal, the key comprising a plurality of scale degrees, each scale degree having a scale degree frequency; and the first beat frequency is equal to a first scale degree frequency of the key, the first scale frequency being further based on the proximity of the first scale degree frequency to a desired beat frequency.

According to a further aspect which can be combined with other embodiments disclosed herein, there is provided a non-transitory processor-readable medium containing instructions executable by a processor to carry out the method steps above.

According to a further aspect which can be combined with other embodiments disclosed herein, there is provided a non-transitory storage medium containing music data created using the methods above.

BRIEF DESCRIPTION OF THE DRAWINGS

Embodiments will now be described by way of examples with reference to the accompanying drawings, in which like reference numerals may be used to indicate similar features, and in which:

FIG. 5A is a frequency-domain graph of an example unmodified music signal showing a set of filters applied to it to generate audio signal components and beat components generated at specific frequencies for mixing with the unmodified music signal according to example embodiments described herein.

DETAILED DESCRIPTION OF EXAMPLE EMBODIMENTS

Figure 1:
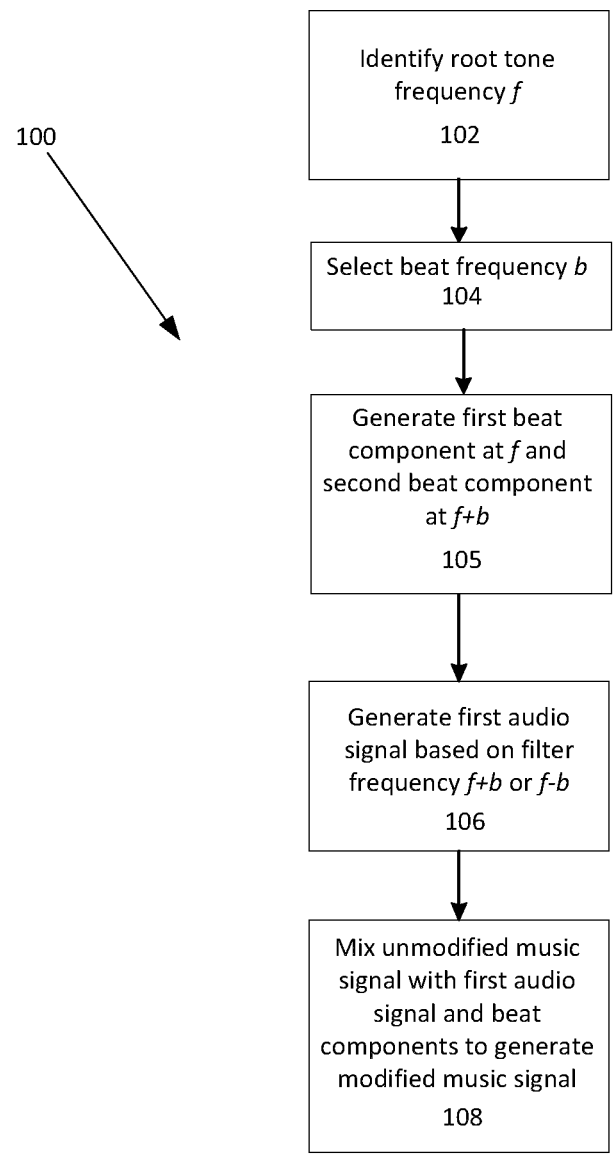
FIG. 1 is a flowchart of an example method for integrating binaural and monaural beats with music according to example embodiments described herein.

Example embodiments will now be described with respect to methods, devices, and non-transitory media for creating or storing music with integrated auditory beat stimuli. By integrating ABS signals with music using the techniques described and claimed herein, it may be possible in some embodiments to mask the ABS stimuli to render them less overt and noticeable and/or to render them more pleasant to subjects. This masking may facilitate longer and more frequent use of the ABS stimuli by subjects, and may allow the stimuli to be presented to subjects in any context where music would be appropriate. Techniques are described for integrating monaural beats, binaural beats, or a combination of monaural and binaural beats into music. Music integrating binaural beats would typically be encoded as a stereo audio signal capable of being presented to a user's ears independently (e.g. through stereo headphones or earbuds), while music using monaural beats could be encoded as a stereo or mono audio signal and could be effectively presented to a subject using broadcast or ambient channels (e.g. loudspeakers). Music integrating both monaural and binaural beats could be presented through either modality and could potentially be effective in either scenario.

The techniques described herein make use of musical analysis of the pre-existing or generated music used for the integration of the ABS stimuli. Some basic concepts from music theory are discussed briefly to provide context for the description that follows.

A music composition's "key" is a group of pitches, or "scale", that forms the framework of that composition's harmonic and melodic structure. The "root tone" is the fundamental pitch of any harmonic group of pitches consisting of two or more notes (a "chord"). These notes could be played on their own and reflect the harmonic sequence of a music composition.

When produced, root tones are able to sound in sync with all other melodic and harmonic elements of the music composition or song. When introducing sound elements into a song that match the root tones and/or the notes of a chord based on that root tone, the introduced stimulus may remain in sync with the melodic and harmonic elements of the song and avoid introducing noise perceived by a listener as dissonant.

There are a number of audio tools that provide real-time analysis of a song's key, chord progression and root tone frequencies. These audio tools may include software and hardware units. Two examples of software tools for key detection are Superpowered (https://superpowered.com/) and Mixed In Key (https://mixedinkey.com/). In some cases, the chord progression and/or root tone frequencies of a song may be determined based on key detection. Typically, music theory dictates that the root tone is the first tone of a key's scale.

The techniques described herein may in some embodiments be implemented using one or more known audio analysis and synthesis tools and techniques. These tools and techniques may include audio equalization and equalizers, audio mixing and mixers, and real-time audio analysis and analyzers.

Audio equalization (or simply "equalization") is a term used to denote the process of attenuating the levels (i.e. amplitude) of different frequencies in an audio signal. It can be applied through both hardware and software tools, such as rack-mount audio units, VST software plugins, and components in a vehicle's control panel. Equalizers may comprise a variety of audio filters that process audio in the frequency domain. They may include shelving filters, band-pass filters, band-reject filters, high-pass filters, high-shelf filters, low-pass filters, and low-shelf filters. They are commonly applied in the sound recording process to improve an audio track's sound or make certain audio mix components sound more or less prominent. In the context of the described embodiments, an equalizer may be used not only to alter the frequency range of the recording to support specific brainwave entrainment frequencies, but also to create artifacts within the music that stimulate ABS. As one example, an audio track (such as a music track) may be fed through a band-pass filter centered at 100 Hz in one ear, and fed through a bandpass filter centered at 120 Hz in another ear, thereby creating auditory artifacts within the audio track to lightly stimulate a 20 Hz "beat" frequency.

An audio mixer is an audio unit that combines multiple tracks of sound into one or more tracks or channels. This unit also provides the ability to attenuate the volumes of each prospective track. In the described embodiments, a mixer may be used to combine an original (unmodified) audio file or audio signal with an equalized version of that file or signal, as well as with one or more oscillators used to produce ABS stimuli, to produce a modified music file or signal containing integrated ABS stimuli.

A real-time analyzer is an audio unit that measures the frequency spectrum of an audio signal. It is generally a frequency spectrum analyzer that is able to process audio in real time. This analysis may in some embodiments be used to determine root tones and keys of a piece of music, either for a piece of music as a whole or for a given moment within a piece of music. In other embodiments, key detection and/or root tone detection may be performed by a separate hardware or software module, such as the examples of key detection software described above.

Some of these tools or techniques may be implemented using software running on a processor, such as that of a general-purpose computer, or on specialized audio processing hardware. In some embodiments, the various steps of the described methods or processes may be performed by separate hardware units, such as some steps being performed by a local computer and the other steps being performed by a cloud computing server in real-time or asynchronous communication with the local computer over a network.

In the context of the described embodiments, the fundamental or center frequency of a synthesized ABS stimulus may be referred to herein as its "synthesis frequency". This may denote, for example, the centre frequency of a band-pass filter output, the high-end cut-off frequency of a low-pass filter, or the frequency of a synthesized sine wave when any of these components is used for ABS. The entrainment frequency of a pair of ABS stimuli would therefore be equal to the delta between the synthesis frequencies of the first and second channels. Presenting the first and second channels to a subject would generate the perception of a beat at the delta frequency.

A first example embodiment of a method 100 for integrating auditory beat stimuli into music will now be described with reference to FIG. 1. The method operates on an unmodified music signal 502, which could be provided in the form of a signal received over a communication link, a digital file stored in a memory, or a music signal generated on the fly by a processor. This example and the subsequent described examples draw example frequencies from the A440 or A4 pitch standard whereby scale degree "A4" is tuned to 440 Hz, as shown in detail at (https://pages.mtu.edu/~suits/notefreqs.html), which is hereby incorporated by reference in its entirety. However, these examples are not intended to be limiting and other embodiments could use a different pitch standard.

At step 102, a root tone frequency of the unmodified music signal 502 is identified. This step may be implemented by a real-time analyzer in some embodiments. The root tone frequency is the frequency of the root tone of the unmodified music signal 502 within a selected octave: for example, if the root tone of a song is "F", then the root tone frequency is a frequency selected from of one of the "F" notes within the A440 pitch standard, such as "F0" (21.83 Hz), "F1" (43.65 Hz), and so on through "F8" (5587.65 Hz). In the context of the described examples, the root tone frequency of a music signal may be denoted as f in equations.

Once the root tone is selected (for example, 349.23 Hz corresponding to root tone "F4"), at step 104 a first beat frequency is selected. This first beat frequency corresponds to the desired entrainment frequency for the ABS process. Potential entrainment frequencies for different applications are detailed in various publications relating to research on the cognitive effects of ABS. For example, beat frequencies of 1, 3, 4, 5, 6, 6.66, 7, 10, 15, 20, 30, 39, 40, 41, and 45 Hz, among others, are described in the Chaieb paper in the context of studies of the cognitive effects of ABS. In some embodiments, a beat frequency may be used that varies over time in order to assist the entrainment process. In the context of the described examples, the beat frequency of a music signal may be denoted as b in equations.

At step 105, a first beat component 508 is generated having a frequency equal to the root tone frequency 540 $f$, and a second beat component 509 is generated having a frequency equal to the root tone frequency 540 shifted by the beat frequency 660 $b$ to yield f+b (or f−b). In some embodiments, the first and second beat components 508, 509 are pure sine waves of frequencies f and f+b respectively. In other embodiments, the first and second beat components 508, 509 may have other waveform characteristics, such as more complex waveforms having their respective frequency peaks at frequencies f and f+b respectively and spanning a non-zero bandwidth in the frequency domain. In some embodiments, the first and second beat components 508, 509 may be generated by two or more oscillators based on root tone and/or key data derived from the unmodified music signal 502, and/or desired beat frequency data supplied based on an intended entrainment application.

At step 106, a first audio signal 504 is generated. The first audio signal 504 is intended to encode an ABS stimulus with a synthesis frequency displaced (shifted) from the root tone in the frequency domain by a distance equal to the beat frequency. Thus, if the unmodified music signal 502 has a root tone frequency of f, then the synthesis frequency of the first audio signal 504 is f+b (or f−b). The purpose of this first audio signal 504 is to provide a signal that, when combined with the unmodified music signal 502, generates a monaural and/or binaural beat with frequency b due to the delta b between unmodified music signal 502 root tone frequency f and first audio signal 504 synthesis frequency f+b (or f−b).

The first audio signal 504 may be generated by selecting a first portion of the unmodified music signal 502 lying within a first frequency range. This first frequency range may be based on a first filter frequency, such as the center frequency of a band-pass filter or the high-end cut-off frequency of a low-pass filter. The first filter frequency f+b (or f−b) is equal to the root tone frequency f shifted by the first beat frequency b. Thus, in this case, the first filter frequency operates as the synthesis frequency of the first audio signal 504.

At step 108, the unmodified music signal 502 is mixed with the first beat component 508, second beat component 509, and first audio signal 504 to produce a modified music signal 620. This mixing may be within a single track or channel to produce a mono audio signal, or between two channels or tracks to produce a stereo audio signal. For example, to produce a stereo signal, a first channel of the unmodified music signal 502 mixed with an equalized version of the first audio signal 504 and second beat component 509 could be used to generate a first channel intended for a subject's left ear, while a second channel of the unmodified music signal 502 could be mixed with the first beat component 508 to generate the second channel intended for the subject's right ear. As described above, this mixing step 108 results in a monaural and/or binaural beat with frequency b due to the delta b between first beat component 508 at synthesis frequency f and second beat component 509 at synthesis frequency f+b (or f−b). This beat may be masked by the correlation to unmodified music signal 502 root tone frequency f and first audio signal 504 synthesis frequency f+b (or f−b).

The basic method 100 described above thus uses the root tone of a music signal as one of the synthesis frequencies for the ABS stimuli. This basic technique can be further refined to assist in integrating the ASB stimuli into the music signal.

Figure 2:
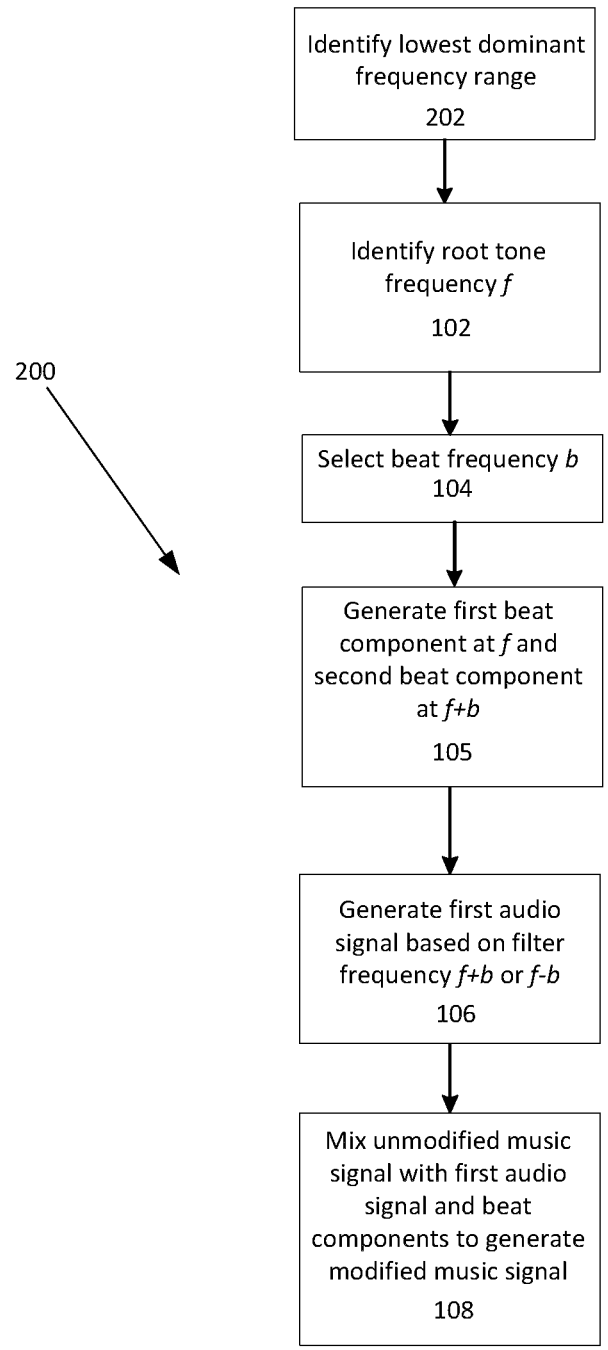
FIG. 2 is a flowchart of a second example method for integrating binaural and monaural beats with music according to example embodiments described herein.

In some embodiments, such as the expanded method 200 shown in FIG. 2, step 102 is premised on a further step 202 of identifying a lowest dominant frequency range of the unmodified music signal 502 based on the lowest dominant frequency range of the music signal. Frequency analysis (such as real-time analysis) of the music signal may be used to determine the lowest dominant frequency or lowest spectral range with a significant mix presence in the music signal. This lowest frequency range may then be used to constrain the choice of root tone frequency: for example, in the above example wherein the root tone of the unmodified music signal 502 is "F", the lowest dominant frequency range may be identified as being 100-200 Hz. This constrains the choice of root tone frequency to the range of 100-200 Hz, yielding only a single "F" option, "F3", with root tone frequency 174.61 Hz.

In some embodiments, the method 200 may further comprise a step 204 of identifying a key of the unmodified music signal 502. As described above with reference to basic music theory, the key of a musical composition (e.g. the key of the song is "C") comprises a plurality of scale degrees or scale tones (e.g. "E0" is a scale tone within key "C"), and each scale degree has a scale degree frequency within the pitch standard being used ("E0"=20.60 Hz in pitch standard A440). In the presently described method 200, the first beat frequency b is selected by choosing a first scale degree frequency (e.g. 20.60 Hz for "E0") within the key (e.g. "C") based on the proximity of the first scale degree frequency (20.60 Hz) to a desired beat frequency (e.g., an application of ABS may dictate the use of an entrainment frequency of 20 Hz). Thus, given the example musical and entrainment properties set out above, the method 200 would select "E0" as the scale degree in key "C" having a scale degree frequency (20.60 Hz) most proximate to the desired beat frequency (entrainment frequency 20 Hz). Given a root tone frequency of 184.61 Hz ("F3"), this would result in a first filter frequency of (174.61+/−20.60 Hz)=195.21 Hz or 154.01 Hz. When combined with the unmodified music signal 502, this would yield a monaural and/or binaural beat at beat frequency 20.60 Hz, effecting a brainwave entrainment frequency at 20.60 Hz.

In a second illustrative example using the same piece of music in the key of "C" as above, the desired entrainment frequency is 16 Hz instead of 20 Hz. In this case, the scale tone of key "C" closest to 16.35 Hz is scale degree "C0", having a scale degree frequency of 16.35 Hz in pitch standard A440. Thus, the "C0" scale degree frequency of 16.35 Hz would be selected as the beat frequency. The music would be mixed and equalized as described above to integrate monaural and/or binaural beats based on the selected beat frequency 16.35 Hz, e.g. by using a first filter frequency of (174.61+/−16.35 Hz)=190.96 Hz or 158.26 Hz.

Tables 1 and 2 below provide examples of generating either monaural beats or binaural beats using the techniques and example parameters described above. Monaural beats, as shown in Table 1, may be generated using a first layer ("Layer 1") comprising the unmodified music signal 502 (or an equalized version thereof), mixed with a second layer ("Layer 2") comprising the first audio signal 504 (synthesized at frequency f+b).

TABLE 1

| Monaural Beats only | |
| --- | --- |
| Monaural Beats - Layer 1 | Synthesis Frequency: f (Hz) |
| Monaural Beats - Layer 2 | Synthesis Frequency: f + b (Hz) | f = Determined by root tone and spectral data e.g. if the root tone is "F" and the lowest dominant frequency range is 100-200 Hz, f = 174.61 Hz (if A4 = 440 Hz)
b = Lowest scale degree near the desired "beat" frequency - provided by key information e.g. if the desired entrainment frequency is 20 Hz, the song is in the key of C and the lowest scale tone is E0, b would be = to 20.60 Hz Binaural beats, as shown in Table 2, may be generated using a first channel ("Channel 1", presented to e.g. a subject's left ear) comprising the first audio signal 504 (synthesized at frequency f+b), mixed with a second channel ("Channel 2", presented to e.g. a subject's right ear) comprising the unmodified music signal 502 (or an equalized version thereof).

TABLE 2

| Binaural Beats only | |
| --- | --- |
| Binaural Beats - Channel 1 | Synthesis Frequency: f + b (Hz) |
| Binaural Beats - Channel 2 | Synthesis Frequency: f (Hz) | f = Determined by root tone and spectral data e.g. if the root tone is "F" and the lowest dominant frequency range is 100-200 Hz, f = 174.61 Hz (if A4 = 440 Hz)
b = Lowest scale degree near the desired "beat" frequency - provided by key information i.e. if the desired entrainment frequency is 20 Hz, the song is in the key of C and the lowest scale tone is E0, b would be = to 20.60 Hz
NOTE:
If 0.5f is greater than 80 Hz, take it down one octave (i.e. instead of 0.5f, use 0.25f)

Figure 3:
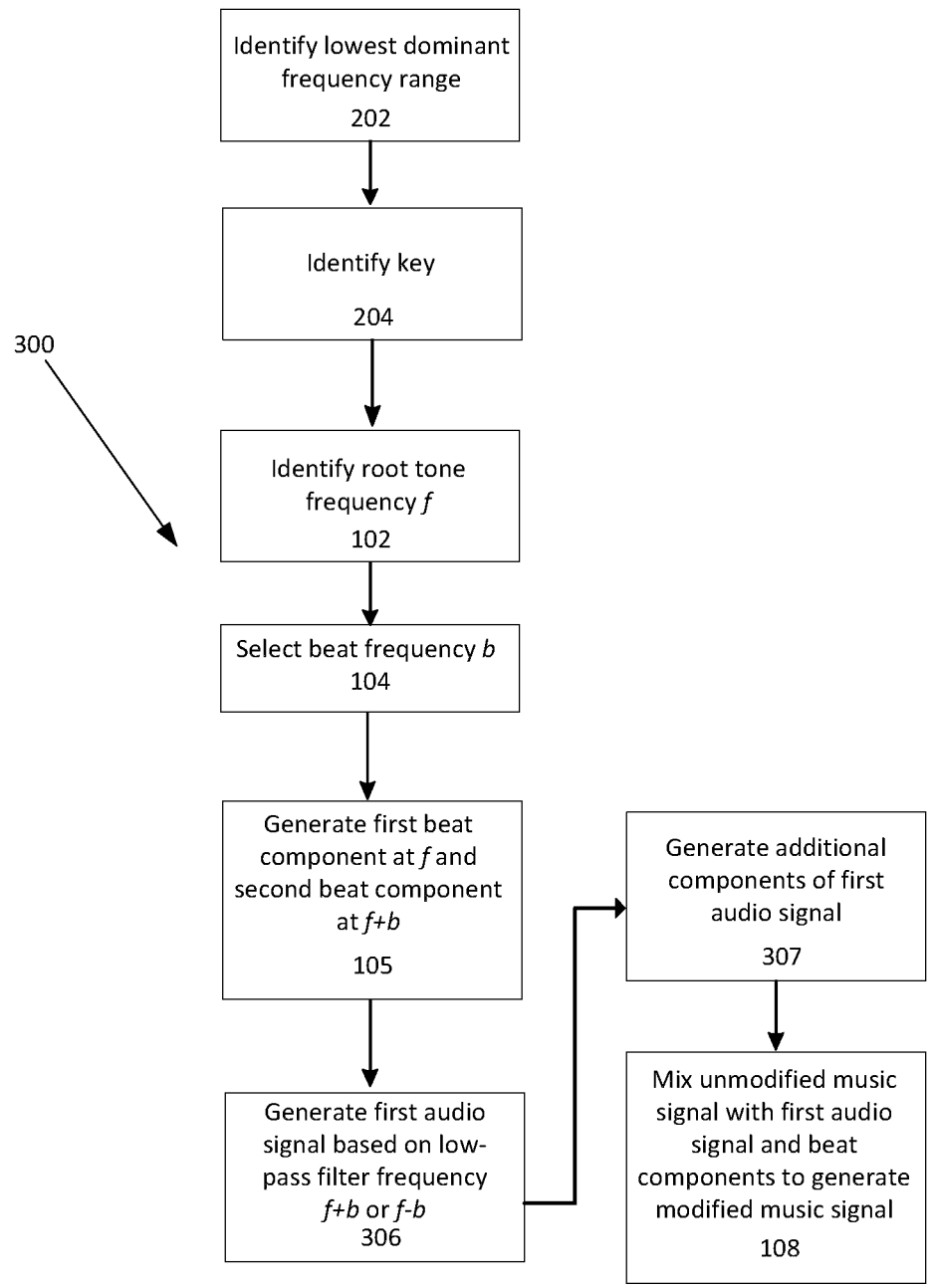
FIG. 3 is a flowchart of a third example method for integrating binaural and monaural beats with music according to example embodiments described herein.

In some embodiments, particularly embodiments used to generate monaural beats, the first audio signal 504 may be generated by applying to the unmodified music signal 502 a low-pass filter with a high-end cut-off frequency equal to the first filter frequency (e.g. 192.21 Hz). FIG. 3 shows such a method 300 wherein step 106 is replaced with step 306 using such a low-pass filter extending over a low-pass frequency range.

In some embodiments, additional audio signal components may be added to the first audio signal 504 at step 307 to further assist in integrating the ABS stimuli into the music signal. Where the first audio signal 504 is generated using a low-pass filter (such as certain embodiments used to generate monaural beats), these additional audio signal components may comprise the output of one or more band-pass filters having center frequencies harmonic with the filter frequency of the low-pass filter. For example, one or more band-pass filters may be centered on frequencies that are one or two octaves higher than the next lowest filter frequency. In some embodiments, these band-pass filters have center frequencies (denoted as the filter frequency for a band-pass filter) that are each two octaves higher than the next lowest filter frequency, i.e., the filter frequency of each band-pass filter is equal to four times the frequency of the next lowest filter frequency (because moving one octave higher doubles the frequency of a tone, so, e.g., whereas "A4"=440 Hz, and "A5" is one octave up from "A4", "A5"=880 Hz).

Table 3 below illustrates the filter frequencies used in an example method for generating monaural beats. Four filters are applied to the unmodified music signal 502: a low-pass filter 512 with a filter frequency (i.e. high-end cut-off frequency) of f+b, and three band-pass filters having center frequencies each positioned two octaves above the previous filter, i.e., a first band-pass filter 514 at center frequency 4(f+b), a second band-pass filter 516 at center frequency 16(f+b), and a third band-pass filter 518 at center frequency 64(f+b).

TABLE 3

Monaural Beats only

| | Low-Pass Filter 512 | Band-Pass Filter 514 | Band-Pass Filter 516 | Band-Pass Filter 518 |
|---|---|---|---|---|
| Mono Channel (or applied to both stereo channels) | Cut-off Freq: f + b {Hz} | Central Freq: 4 (f + d) {Hz} Low-mid bandwidth | Central Freq: 16 (f + b) {Hz} Low-mid bandwidth | Central Freq: 64 (f + b) {Hz} Mid-high bandwidth |

The outputs of these four filters are then equalized and mixed into the unmodified music signal 502 along with the first beat component 508 and second beat component 509 to generate the modified music signal 620. The root tone of f mixed with the filter output at f+b, and further masked by the harmonics at 4(f+b), 16(f+b), and 64(f+b), may result in a non-dissonant perception of the modified music signal 620 despite the presence of the beat resulting from the first beat component 508 at f and second beat component 509 at f+b. This modified music signal 620 may be transmitted, broadcast, presented to a subject through an audio output device (mono or stereo), or stored as a music data file on a storage medium such as a CD, hard drive, or RAM.

FIG. 5A illustrates an example set of filters 510 applied to the unmodified music signal 502 to generate a first audio signal 504 in accordance with the monaural beat integration method described immediately above and corresponding to Table 3 above. The unmodified music signal 502 is graphed in the frequency domain, with the set of filters 510 shown below it being applied to capture certain frequency ranges associated with each filter. The root tone frequency 540 f of the unmodified music signal 502 is up-shifted by the beat frequency 560 b to yield a first filter frequency 550 of (f+b). This first filter frequency 550 defines a first filter in the form of low-pass filter 512, defining a first frequency range bounded at the high end by first filter frequency 550. A second filter frequency 552, set two octaves up from the first filter frequency 550 at 4(f+b), defines a second filter in the form of a band-pass filter 514, defined by a center frequency equal to the second filter frequency 552. This pattern continues for a third filter (band-pass filter 516) and fourth filter (band-pass filter 518) defined respectively by center frequencies equal to third filter frequency 554 (at 16(f+b)) and fourth filter frequency 556 (at 64(f+b)).

At the bottom left of the figure, the first beat component 508 and second beat component 509 are shown being generated at the root tone frequency 540 and first filter frequency 550 respectively. In this example, the first beat component 508 and second beat component 509 are shown as pure sine waves generated at their respective synthesis frequencies.

Figure 4:
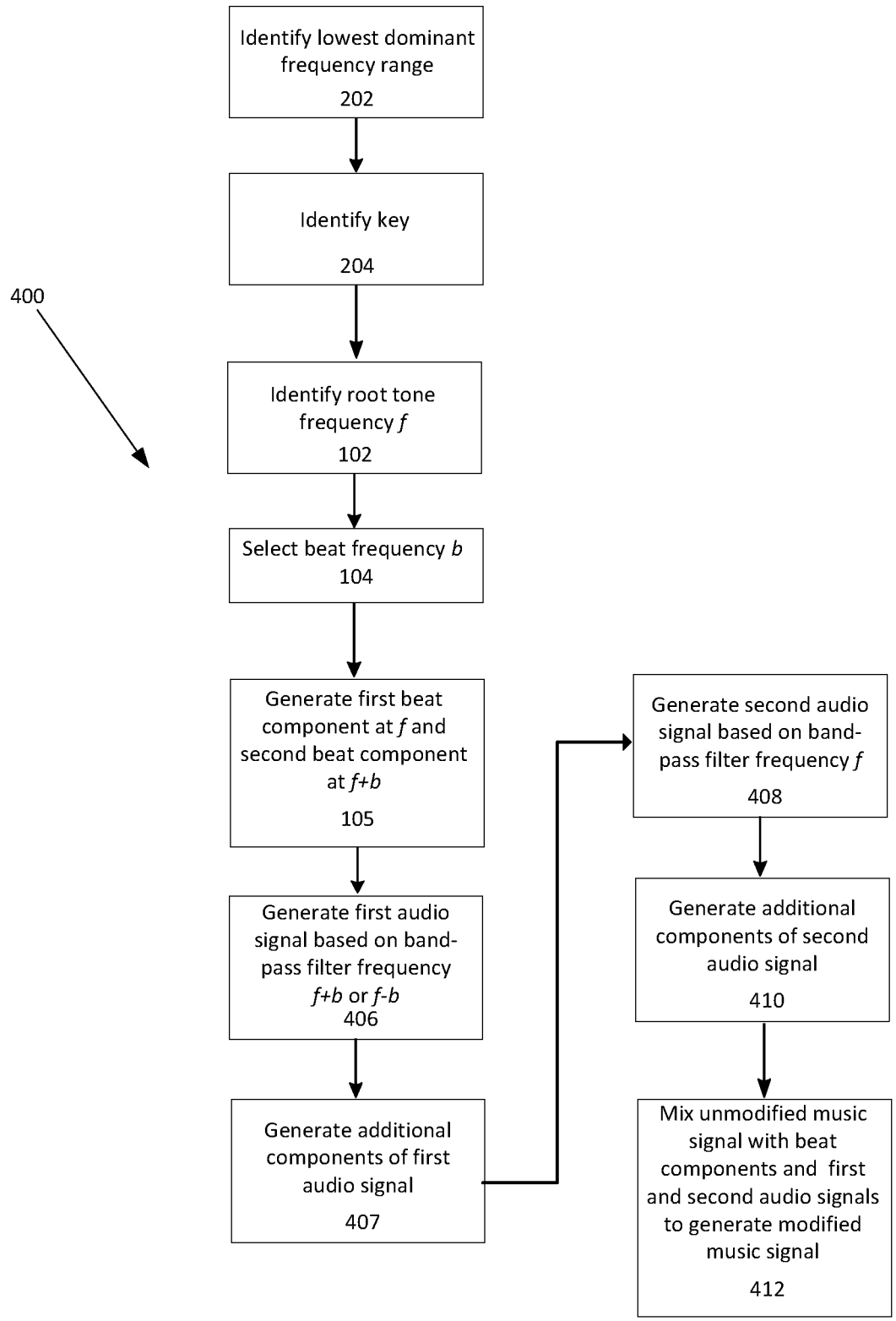
FIG. 4 is a flowchart of a fourth example method for integrating binaural and monaural beats with music according to example embodiments described herein.

In other embodiments, particularly embodiments used to generate binaural beats, the first audio signal 504 may be generated by applying to the unmodified music signal 502 a band-pass filter with a center frequency equal to the first filter frequency (e.g. 192.21 Hz). FIG. 4 shows such a method 400 wherein step 106 is replaced with step 406 using such a low-pass filter extending over a band-pass frequency range.

In some such embodiments, the addition of audio signal components to the first audio signal 504 at step 407 may use not only additional band-pass filters centered on harmonic frequencies above (f+b) as in method 300, but also a low-pass filter with a high-end cut-off frequency (i.e. filter frequency) equal to 0.5f+b, i.e., one octave lower than f, frequency-shifted by b. A further variant could set the low-pass filter frequency to 0.5(f+b) instead of 0.5f+b.

Some such embodiments may also generate a second audio signal 506 at step 408 for mixing with the unmodified music signal 502. Whereas the first audio signal 504 is mixed with the unmodified music signal 502 to generate a first channel of the modified music signal 620 (intended for e.g. the left ear), the second audio signal 506 is mixed with the unmodified music signal 502 to generate a second channel of the modified music signal 620 (intended for e.g. the right ear). The second audio signal 506 contains harmonics based on the synthesis frequency f in order to enhance the binaural beat effect in conjunction with the first audio signal 504 generated with synthesis frequency f+b. The generation of these additional harmonics or other components takes place at step 410. At step 412, the first audio signal 504 and second audio signal 506 are mixed with the first beat component 508, second beat component 509, and unmodified music signal 502 as described above to produce the modified music signal 620.

Table 4 below illustrates the filter frequencies used in an example method for generating binaural beats. A set of five filters 530 is applied to the unmodified music signal 502: a low-pass filter 532 with a filter frequency (i.e. high-end cut-off frequency) of 0.5f+b, a band-pass filter 534 at center frequency f+b (i.e. the first filter frequency), and three additional band-pass filters having center frequencies each positioned two octaves above the previous filter, i.e., a second band-pass filter 536 at center frequency 4(f+b), a third band-pass filter 538 at center frequency 16(f+b), and a fourth band-pass filter 539 at center frequency 64(f+b). These five filter are applied to the unmodified music signal 502 to generate the first audio signal 504.

The second audio signal 506 is generated using a similar set of five filters, but based on a synthesis frequency of f instead of f+b. Thus, the low-pass filter 522 has a filter frequency of 0.5f, the first band-pass filter 524 has center frequency f (i.e. the root tone frequency 540), and the three additional band-pass filters have center frequencies each positioned two octaves above the previous filter, i.e., a second band-pass filter 526 at center frequency 4f, a third band-pass filter 528 at center frequency 16f, and a fourth band-pass filter 529 at center frequency 64f. These five filter are applied to the unmodified music signal 502 to generate the second audio signal 506.

TABLE 4

Binaural Beats only

|  | Low-Pass Filter 532 | Band-Pass Filter 534 | Band-Pass Filter 536 | Band-Pass Filter 538 | Band-Pass Filter 539 |
|---|---|---|---|---|---|
| Stereo Channel 1 (L/R ear) | Cut-off Freq: 0.5f + b {Hz} | Central Freq: f + b {Hz} Low-mid bandwidth | Central Freq: 4 (f + b) {Hz} Low-mid bandwidth | Central Freq: 16 (f + b) {Hz} Low-mid bandwidth | Central Freq: 64 (f + b) {Hz} Mid-high bandwidth |
|  | Low-Pass Filter 522 | Band-Pass Filter 524 | Band-Pass Filter 526 | Band-Pass Filter 528 | Band-Pass Filter 529 |
| Stereo Channel 2 (L/R ear) | Cut-off Freq: 0.5f {Hz} | Central Freq: f {Hz} Low-mid bandwidth | Central Freq: 4f {Hz} Low-mid bandwidth | Central Freq: 16f {Hz} Low-mid bandwidth | Central Freq: 64f {Hz} Mid-high bandwidth |

The outputs of these five filters are then equalized and mixed into the unmodified music signal 502 and the first audio signal 504 to generate the modified music signal 620. In the case of binaural beats, this mixing comprises mixing the first audio signal 504 with the unmodified music signal 502 to generate a first channel (Stereo Channel 1) of the modified music signal 620, and mixing the second audio signal 506 with the unmodified music signal 502 to generate a second channel (Stereo Channel 2) of the modified music signal 620.

Figure 5B:
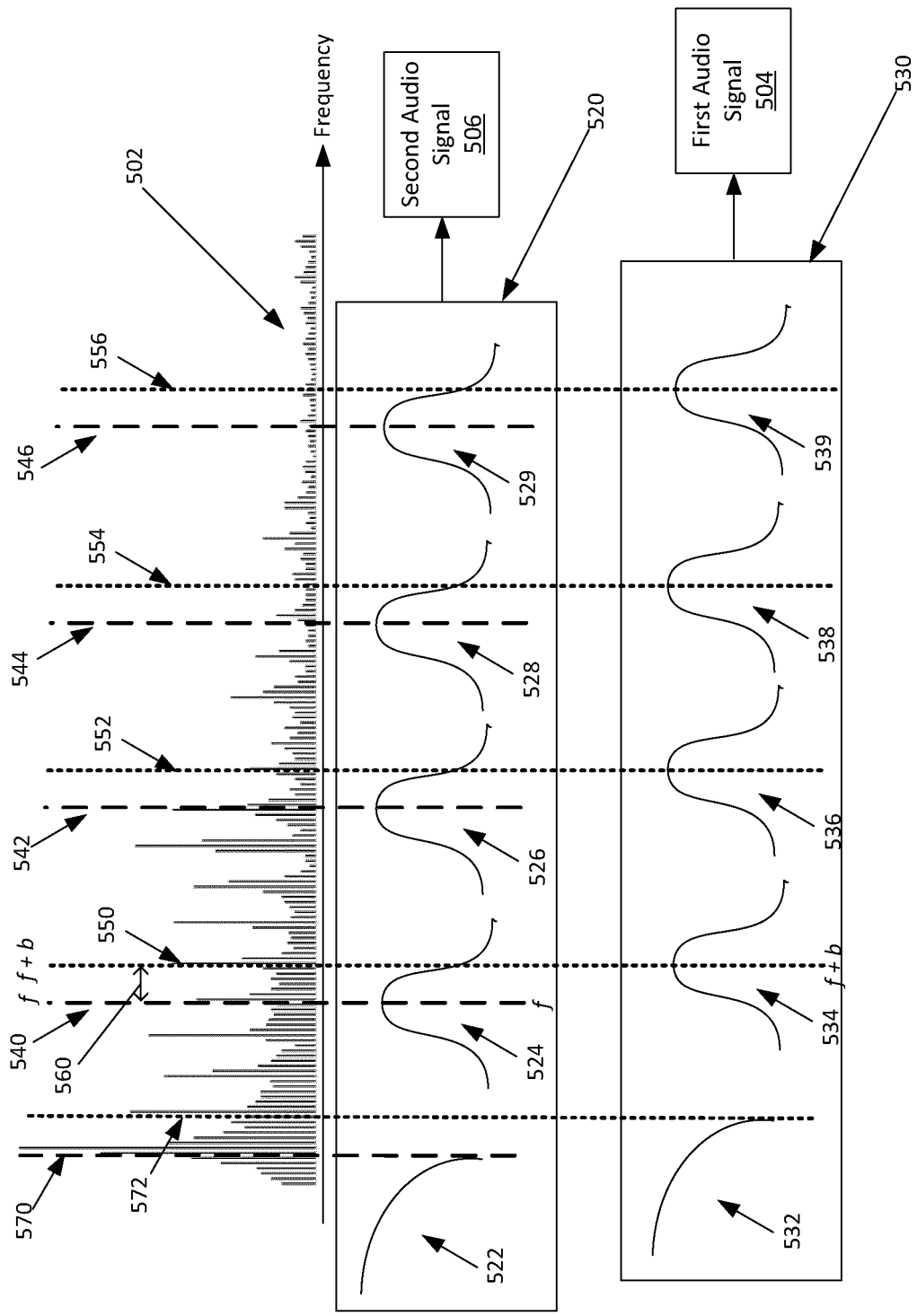
FIG. 5B is a frequency-domain graph of an example unmodified music signal showing two sets of filters applied to it to generate audio signal components generated at specific frequencies for mixing with the unmodified music signal according to example embodiments described herein.

FIG. 5B is analogous to FIG. 5A, but illustrates an example generation of binaural instead of monaural beats. FIG. 5B shows an example first set of filters 530 applied to the unmodified music signal 502 to generate a first audio signal 504, and a second set of filters 520 applied to the unmodified music signal 502 to generate a second audio signal 506, in accordance with the binaural beat integration method described immediately above and corresponding to Table 4 above.

First, the generation of the first audio signal 504 in FIG. 5B is described. The root tone frequency 540 $f$ of the unmodified music signal 502 is up-shifted by the beat frequency 560 $b$ to yield a first filter frequency 550 of (f+b). This first filter frequency 550 defines a first filter in the form of band-pass filter 534, defining a first frequency range centred on first filter frequency 550. A low-pass filter frequency 570 is set at half the root tone frequency 540, or 0.5f. This low-pass filter frequency 570 is shifted right in the frequency domain by the amount of the beat frequency 660 $b$ to yield another low-pass filter frequency 572 at 0.5f+b. This second low-pass filter frequency 572 defines a low-pass filter 532, defining a frequency range bounded at the high end by filter frequency 572. Moving in the high-frequency direction from the first band-pass filter 534, a second band-pass filter 536 is set two octaves up from the first filter frequency 550 at second band-pass filter frequency 552 at 4(f+b). This pattern continues for a third band-pass filter (band-pass filter 538) and fourth band-pass filter (band-pass filter 539) defined respectively by center frequencies equal to filter frequency 554 (at 16(f+b)) and fourth filter frequency 556 (at 64(f+b)).

Finally, the generation of the second audio signal 506 in FIG. 5B is described. The second audio signal 506 is generated by a second set of filters 520. The root tone frequency 540 $f$ defines a first filter in the form of band-pass filter 524, defining a first frequency range centred on root tone frequency 540 at f. A low-pass filter frequency 570 is set at half the root tone frequency 540, or 0.5f. This low-pass filter frequency 570 defines a low-pass filter 522, defining a frequency range bounded at the high end by filter frequency 570. Moving in the high-frequency direction from the first band-pass filter 524, a second band-pass filter 526 is set two octaves up from the root tone frequency 540 at second band-pass filter frequency 542 at 4f. This pattern continues for a third band-pass filter (band-pass filter 528) and fourth band-pass filter (band-pass filter 529) defined respectively by center frequencies equal to filter frequency 544 (at 16f) and fourth filter frequency 546 (at 64f).

The techniques described above may be combined and/or modified to produce music tracks integrating both monaural and binaural beats. Such combined beats may be more effective than either type of beat in isolation when presented to a subject in stereo (e.g. with one channel to each ear). They may also be more versatile, e.g., they may allow the same music track to entrain subjects when presented either in stereo (binaural+monaural beats effective) or in mono (only monaural beats effective).

Tables 5 and 6 below set out example filter parameters used in an example method for integrating both monaural and binaural beats into a music signal. Like the binaural beat generation method described above with reference to Table 4 and FIG. 5B, the example method below uses two low-pass filters with filter frequencies 0.5f and 0.5f+b. In this example, however, the low-pass filter frequencies are intended to be lower than a low-pass filter frequency maximum, in this example 80 Hz. If the root tone frequency f is above 160 Hz, i.e. the low-pass filter frequency 0.5f is above 80 Hz, then instead of using 0.5f and 0.5f+b the low-pass filter frequencies are instead set to 0.25f and 0.25f+b.

The example method parameters shown in Tables 5 and 6 also present two alternative methods of setting the filter frequencies for the higher-frequency harmonics: the high-frequency components of the first audio signal 504 may either use the values provided in the binaural beat method of Table 4, i.e. 4(f+b), 16(f+b), and 64(f+b), or they can alternatively use the values 4f+b, 16f+b, and 64f+b. Some embodiments multiply the root tone frequency (e.g. 4f) by a power of two (or four) to change the octave before shifting by the beat frequency (e.g. +b); other embodiments multiply the frequency (e.g. times 4) after shifting the root tone frequency by the beat frequency (to yield (f+b)).

TABLE 5

Monaural and Binaural Beats

| Binaural Beats - Channel 1 | Synthesis Frequency: f + b (Hz) |
|---|---|
| Binaural Beats - Channel 2 | Synthesis Frequency: f (Hz) |

TABLE 5-continued

Monaural and Binaural Beats

| | |
|---|---|
| Monaural Beats - Layer 1 | Synthesis Frequency: 0.5f (Hz) → Max = 80 Hz |
| Monaural Beats - Layer 2 | Synthesis Frequency: 0.5f + b (Hz) → Max = 80 Hz | f = Determined by root tone and spectral data e.g. if the root tone is "F" and the lowest dominant frequency range is 100-200 Hz, f = 174.61 Hz (if A4 = 440 Hz)
b = Lowest scale degree near the desired "beat" frequency - provided by key information i.e. if the desired entrainment frequency is 20 Hz, the song is in the key of C and the lowest scale tone is E0, b would be = to 20.60 Hz
NOTE:
If 0.5f is greater than 80 Hz, take it down one octave (i.e. instead of 0.5f, use 0.25f)

TABLE 6

Monaural and Binaural Beats

| | Low-Pass Filter | Band-Pass Filter | Band-Pass Filter | Band-Pass Filter | Band-Pass Filter |
|---|---|---|---|---|---|
| Channel 1 (L/R ear) | Cut-off Freq: 0.5f + b {Hz} 0.25f + b if 0.5f > 80 Hz | Central Freq: f + b {Hz} Low-mid bandwidth | Central Freq: 4 (f + b) {Hz} OR Central Freq: 4f + b {Hz} Low-mid bandwidth | Central Freq: 16 (f + b) {Hz} OR Central Freq: 16f + b {Hz} Low-mid bandwidth | Central Freq: 64 (f + b) {Hz} OR Central Freq: 64f + b {Hz} Mid-high bandwidth |
| | Low-Pass Filter | Band-Pass Filter | Band-Pass Filter | Band-Pass Filter | Band-Pass Filter |
| Channel 2 (L/R ear) | Cut-off Freq: 0.5f {Hz} 0.25f if 0.5f > 80 Hz | Central Freq: f {Hz} Low-mid bandwidth | Central Freq: 4f {Hz} Low-mid bandwidth | Central Freq: 16f {Hz} Low-mid bandwidth | Central Freq: 64f {Hz} Mid-high bandwidth |

The examples of combined monaural beats and binaural beats presented in Tables 5 and 6 above further diverge from the previously-described methods by introducing the use of multiple synthesis frequencies to generate the beats themselves. For example, as set out in Table 5, the binaural beats may be synthesized at synthesis frequencies f and f+b and mixed into the left and right channels of the modified music signal 620, while the monaural beats may be synthesized at frequencies 0.5f and 0.5f+b (or 0.25f and 0.25f+b) and layered over each other by the mixer into both stereo channels. This may in some embodiments require the use of more than two oscillators to generate the required number of different beat components: in this example, four beat components would be added to the music at f, f+b, 0.5f, and 0.5f+b (or 0.25f and 0.25f+b), requiring four beat components generated by four oscillators instead of simply a first beat component 508 and second beat component 509. This use of more than two beat components may be applied in some embodiments to the generation of binaural or monaural beats on their own.

In further embodiments, the methods described above may further apply a high-pass filter to the unmodified music signal 502 to generate the first audio signal 504 and/or second audio signal 506.

The various described methods may be carried out in real time (such as using an automated software or hardware system for analyzing and modifying audio data) or asynchronously (such as by using a digital audio workstation).

Thus, these integration methods leverage the already-existing frequencies of a music recording or live track and turn them into supporting elements for ABS.

Figure 6:
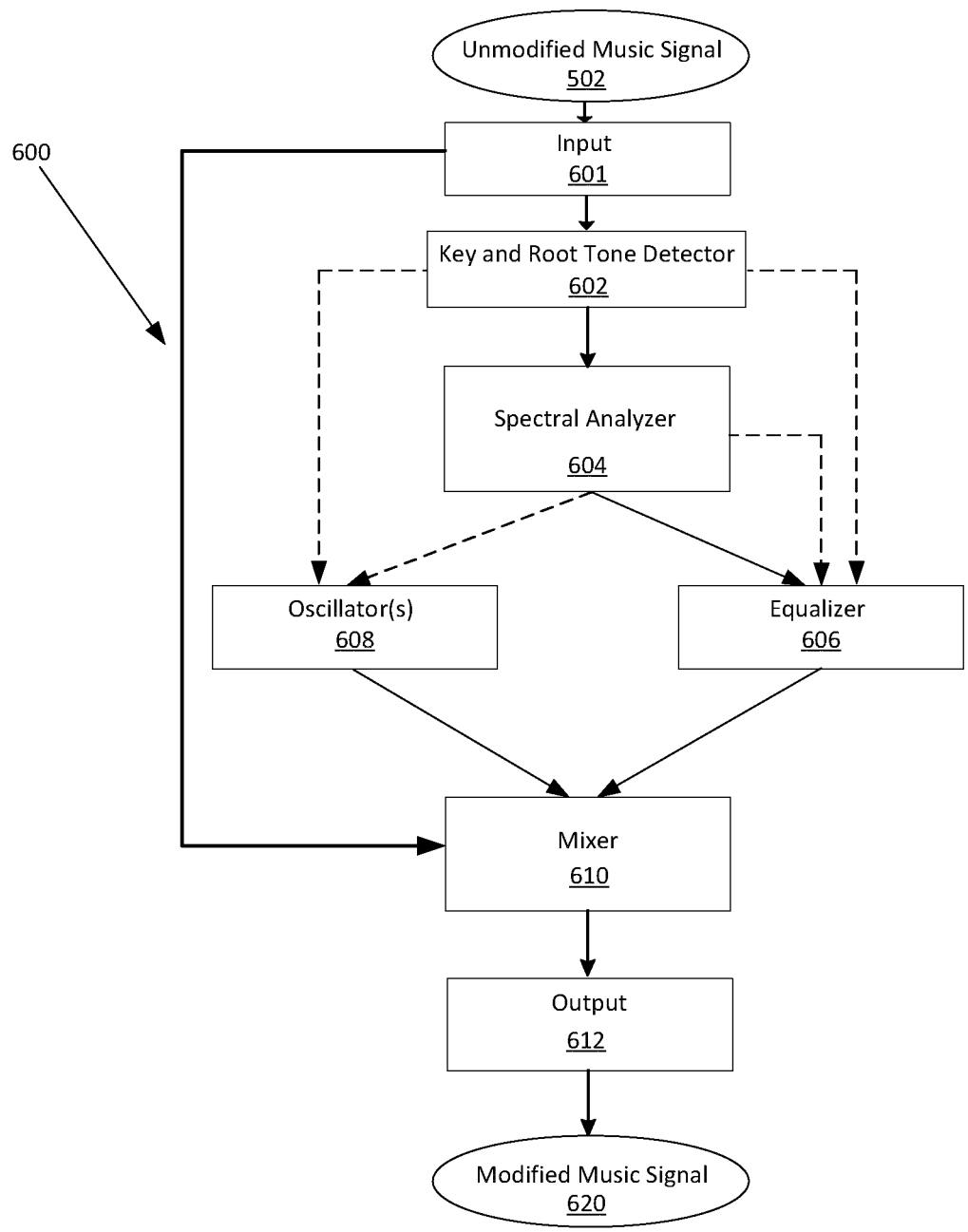
FIG. 6 is a block diagram of an example device for integrating binaural and monaural beats with music according to example embodiments described herein.

As previously discussed, the methods described above may be implemented using audio processing hardware, software, and/or firmware. FIG. 6 illustrates a block diagram of an example audio processing device 600 for integrating auditory beat stimulation stimuli into music according to the methods described above.

In FIG. 6, solid lines indicate communication of audio signal, whereas dashed lines indicated communication of data used by the device such as frequency spectrum data, root tone information, key information, and so on.

The device 600 receives the unmodified music signal 502 at an input 601. The input 601 may be an audio input or a data input depending on the nature of the received music signal; for example, if the unmodified music signal 502 is in the form of a file stored on a storage medium (such as a (mono, stereo, binaural, ambisonic, or 5.1 audio file), the input 601 may be a system data bus or other data input, whereas if the unmodified music signal 502 is in the form of analog audio data (such as from a synthesizer, software instrument, or microphone input) the input 601 may be an analog audio input. Other embodiments of the input 601 are possible depending on the form of the unmodified music signal 502 and how it is received by the device 600.

The input 601 conveys the received audio signal to both a mixer 610 and a key and root tone detector 602.

The key and root tone detector 602 processes the audio in real-time and determines the composition's key. It determines harmonic root tones of the unmodified music signal 502 and their changes over time and maps these out before sending this data to the oscillator(s) 608 and the equalizer 606. The key and root tone detector 602 may be implemented in different embodiments as a software module and/or a hardware module capable of determining the key and harmonic root tones of a music signal input.

The spectral analyzer 604 may in some embodiments be a real-time analyzer. It determines the lowest spectral range with a significant mix presence in the unmodified music signal 502 based on the audio signal received from the key and root tone detector 602. This spectral data is then sent to both the oscillator(s) 608 and the equalizer 606.

The oscillator(s) 608 may in some embodiments comprise two or more oscillators producing pure tone sine waves. They produce binaural and/or monaural beats in real-time or asynchronously. The gain of each oscillator 608 is relative to the amplitude of the unmodified music signal 502, based on the data received from the key and root tone detector 602 and spectral analyzer 604. The amplitude of the signal 502 may be determined differently in different embodiments: some embodiments may use the root-mean-squared (RMS) value of a set of samples, others may use the peak amplitude of a set of samples, and others may use other known averaging or aggregating techniques to determine the overall amplitude of the signal 502. The oscillators 608 generate the beats using synthesis frequencies derived from the spectral, key, and root tone analysis of the unmodified music signal 502 according to the synthesis parameters shown in e.g. Tables 1, 3, and 5. For example, if the root tone detected by the key and root tone detector 602 is "F", the oscillators 608 may synthesize an "F" tone that is within the lowest dominant frequency range determined by the spectral analyzer 604.

The equalizer 606 received the audio signal from the spectral analyzer 604 and data from the key and root tone detector 602 and spectral analyzer 604. It uses this data to apply the various filters to generate the first audio signal 504 and/or second audio signal 506 as set out in e.g. Tables 2, 4, and 6. The equalizer 606 applies a low-pass filter, high-pass filter (optional) and band-pass filters to the music signal, as described in detail above.

The mixer 610 combines the unmodified music signal 502 received from input 601, the equalized/filtered signal(s) (e.g. first audio signal 504 and/or second audio signal 506) received from the equalizer 606, and the output of the oscillators 608 together and mixes it down to a combined mono or stereo modified music signal 620. In some embodiments, the mix may be balanced evenly based on the ratio of peak to RMS amplitude values of the received signals. The mixer 610 then sends the modified music signal 620 to an output 612, which may take any of a number of forms depending on the intended output format of the device 600, such as a data output to write the music data to a storage medium or transmit it to another component, or an audio output such as speakers or headphones to present the music to a subject.

By generating one channel with a synthesis frequency equal to the root tone of the unmodified music signal, and a second channel with a synthesis frequency equal to the root tone shifted up or down in the frequency domain by an amount close to the frequency of one of the scale degrees of the song's key, the methods and devices described herein may be able to create modified music signals 620 containing monaural and/or binaural beats that are less noticeable and/or less dissonant to subjects.

Although the present disclosure may be described, at least in part, in terms of methods and devices, a person of ordinary skill in the art will understand that the present disclosure is also directed to the various components for performing at least some of the aspects and features of the described methods, be it by way of hardware components, software or any combination of the two. Accordingly, the technical solution of the present disclosure may be embodied in the form of a software product. A suitable software product may be stored in a pre-recorded storage device or other similar non-volatile or non-transitory computer- or processor-readable medium, including DVDs, CD-ROMs, USB flash disk, a removable hard disk, or other storage media, for example. The software product includes instructions tangibly stored thereon that enable a processing device (e.g., a personal computer, a server, or a network device) to execute examples of the methods or systems disclosed herein.

The skilled person will also appreciate that the output of the methods and devices described above, namely the modified music signal 620 with integrated ABS stimuli, may be stored as music data (such as an audio file) on a storage medium such as non-volatile or non-transitory computer- or processor-readable medium, including DVDs, CD-ROMs, USB flash disk, a removable hard disk, or other storage media. The music may also be stored on other digital or analog storage media appropriate for use in audio applications or audio playback or broadcast devices, such as cassette tapes, vinyl records, or any other storage medium for digital or analog music data.

In the described methods or block diagrams, the boxes may represent events, steps, functions, processes, modules, messages, and/or state-based operations, etc. While some of the above examples have been described as occurring in a particular order, it will be appreciated by persons skilled in the art that some of the steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps may be repeated, as necessary. Elements described as methods or steps similarly apply to systems or subcomponents, and vice-versa. Reference to such words as "sending" or "receiving" could be interchanged depending on the perspective of the particular device.

The above discussed embodiments are considered to be illustrative and not restrictive. Example embodiments described as methods would similarly apply to systems, and vice-versa.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

The invention claimed is:

1. A processor-implemented method for integrating auditory beat stimuli into music, comprising:
   identifying a root tone frequency of an unmodified music signal;
   selecting a first beat frequency based on a desired brainwave entrainment frequency;
   generating a first beat component having a frequency equal to the root tone frequency;
   generating a second beat component having a frequency equal to the root tone frequency shifted by the first beat frequency;
   generating a first audio signal comprising a first portion of the unmodified music signal lying within a first frequency range, the first frequency range comprising a low-pass frequency range with a high-end cut-off frequency equal to a first filter frequency, the first filter frequency being equal to the root tone frequency shifted by the first beat frequency;
   mixing the unmodified music signal with the first audio signal, the first beat component, and the second beat component to produce a modified music signal; and
   presenting music via an audio output device driven by the modified music signal.

2. The method of claim 1,
   further comprising identifying a lowest dominant frequency range of the unmodified music signal,
   wherein the root tone frequency is within the lowest dominant frequency range.

3. A non-transitory processor-readable medium containing instructions for executing the method of claim 2.

4. The method of claim 2,
further comprising identifying a key of the unmodified music signal, the key comprising a plurality of scale degrees, each scale degree having a scale degree frequency,
wherein selecting the first beat frequency comprises selecting a first scale degree frequency of the key based on the proximity of the first scale degree frequency to a desired beat frequency.

5. A non-transitory processor-readable medium containing instructions for executing the method of claim 4.

6. The method of claim 4, wherein:
the modified music signal comprises a stereo music signal having a first channel and a second channel;
the first frequency range comprises a band-pass frequency range with a center frequency equal to the first filter frequency; and
mixing the unmodified music signal with the first audio signal, the first beat component, and the second beat component comprises mixing the unmodified music signal with the second beat component and first audio signal to generate the first channel,
the method further comprising:
generating a second audio signal comprising a second portion of the unmodified music signal lying within a second frequency range, the second frequency range comprising a band-pass frequency range with a center frequency equal to a second filter frequency, the second filter frequency being equal to the root tone frequency; and
mixing the unmodified music signal with the first beat component and second audio signal to generate the second channel.

7. The method of claim 6, wherein:
the first audio signal further comprises a third portion of the unmodified music signal lying within a third frequency range, the third frequency range comprising a low-pass frequency range with a high-end cut-off frequency equal to a third filter frequency, the third filter frequency being equal to half of the root tone frequency shifted by the first beat frequency; and
the second audio signal further comprises a fourth portion of the unmodified music signal lying within a fourth frequency range, the fourth frequency range comprising a low-pass frequency range with a high-end cut-off frequency equal to a fourth filter frequency, the fourth filter frequency being equal to half of the root tone frequency.

8. The method of claim 7, wherein:
the first audio signal further comprises one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency times an integer multiplier, shifted by the first beat frequency; and
the second audio signal further comprises one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

9. The method of claim 8, wherein each integer multiplier is a power of four.

10. The method of claim 6, wherein:
the first audio signal further comprises:
a third portion of the unmodified music signal lying within a third frequency range, the third frequency range comprising a low-pass frequency range with a high-end cut-off frequency equal to a third filter frequency, the third filter frequency being equal to half of the root tone first filter frequency shifted by the first beat frequency; and
one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency times an integer multiplier, shifted by the first beat frequency; and
the second audio signal further comprises:
the third portion of the unmodified music signal; and
one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

11. The method of claim 6, wherein:
the first audio signal further comprises:
a third portion of the unmodified music signal lying within a third frequency range, the third frequency range comprising a low-pass frequency range with a high-end cut-off frequency equal to a third filter frequency, the third filter frequency being equal to half of the root tone frequency shifted by the first beat frequency; and
one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency shifted by the first beat frequency, times an integer multiplier; and
the second audio signal further comprises:
the third portion of the unmodified music signal; and
one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

12. The method of claim 6, wherein:
the first audio signal further comprises:
a third portion of the unmodified music signal lying within a third frequency range, the third frequency range comprising a low-pass frequency range with a high-end cut-off frequency equal to a third filter frequency, the third filter frequency being equal to one quarter of the root tone frequency shifted by the first beat frequency; and one or more first additional portions of the unmodified music signal lying within one or more first additional frequency ranges, the one or more first additional frequency ranges being one or more frequency bands centered on one or more first additional filter frequencies, each of the one or more first additional filter frequencies being equal to the root tone frequency shifted by the first beat frequency, times an integer multiplier; and the second audio signal further comprises:

the third portion of the unmodified music signal; and one or more second additional portions of the unmodified music signal lying within one or more second additional frequency ranges, the one or more second additional frequency ranges being one or more frequency bands centered on one or more second additional filter frequencies, each of the one or more second additional filter frequencies being equal to the root tone frequency times an integer multiplier.

13. The method of claim 1, wherein the first audio signal further comprises:

one or more additional portions of the unmodified music signal lying within one or more additional frequency ranges, the one or more additional frequency ranges being one or more frequency bands centered on one or more additional filter frequencies, each of the one or more additional filter frequencies being equal to the first filter frequency times an integer multiplier.

14. The method of claim 13, wherein each integer multiplier is a power of four.

15. The method of claim 14, wherein the one or more additional filter frequencies comprise three additional filter frequencies having respective integer multipliers of 4, 16, and 64 respectively.

16. A non-transitory processor-readable medium containing instructions for executing the method of claim 1.

17. A non-transitory storage medium containing modified music signal data encoding a modified music signal generated by the method of claim 1.

18. A device for integrating auditory beat stimuli into music, comprising:

a root tone detector for identifying a root tone of an unmodified music signal;

a first oscillator for generating a first beat component having a frequency equal to a root tone frequency, the root tone frequency being based on the root tone;

a second oscillator for generating a second beat component having a frequency equal to the root tone frequency shifted by a first beat frequency, the first beat frequency being based on a desired brainwave entrainment frequency;

an equalizer for applying a first filter to the unmodified music signal to generate a first audio signal comprising a first portion of the unmodified music signal lying within a first frequency range, the first frequency range being based on a first filter frequency, the first filter frequency being equal to the root tone frequency shifted by the first beat frequency; and a mixer for mixing the unmodified music signal with the first audio signal, the first beat component, and the second beat component to produce a modified music signal.

19. The device of claim 18, further comprising a spectral analyzer for identifying a lowest dominant frequency range of the unmodified music signal, wherein the root tone frequency is within the lowest dominant frequency range.

20. The device of claim 19, wherein:

the root tone detector is further configured to identify a key of the unmodified music signal, the key comprising a plurality of scale degrees, each scale degree having a scale degree frequency; and the first beat frequency is equal to a first scale degree frequency of the key, the first scale frequency being further based on the proximity of the first scale degree frequency to a desired beat frequency.

* * * * *